US006265588B1

(12) United States Patent
Müllner et al.

(10) Patent No.: US 6,265,588 B1
(45) Date of Patent: Jul. 24, 2001

(54) ISOXAZOLE AND CROTONAMIDE DERIVATIVES AND THEIR USE AS PHARMACEUTICALS AND DIAGNOSTICS

(75) Inventors: Stefan Müllner, Hochheim; Bernd Kirschbaum, Mainz; Wilfried Schwab, Wiesbaden, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/580,625

(22) Filed: May 30, 2000

Related U.S. Application Data

(62) Division of application No. 09/296,254, filed on Apr. 22, 1999, now Pat. No. 6,121,479, which is a division of application No. 09/012,570, filed on Jan. 23, 1998, now Pat. No. 5,977,151.

(30) Foreign Application Priority Data

Jan. 28, 1997 (DE) .............................. 197 02 988

(51) Int. Cl.$^7$ .......................... C07D 261/08; C07G 3/00; C07G 18/62; C07G 63/48; C08G 8/621; C08G 63/48; C08K 5/15

(52) U.S. Cl. .......................... 548/248; 536/4.1; 536/22.1; 536/123.1; 528/220; 528/228; 528/271; 525/7.1; 525/8; 525/11; 525/30; 525/54.1; 525/540; 524/17; 524/56

(58) Field of Search .......................... 548/248; 525/7.1, 525/8, 11, 30, 54.1, 55, 540; 524/17, 56; 528/220, 228, 271; 536/4.1, 22.1, 123.1

(56) References Cited

U.S. PATENT DOCUMENTS

| | | |
|---|---|---|
| 4,284,786 | 8/1981 | Kämmerer et al. . |
| 4,965,276 | 10/1990 | Bartlett et al. . |
| 5,308,865 | 5/1994 | Bartlett et al. . |
| 5,494,911 | 2/1996 | Bartlett et al. . |
| 5,547,970 | 8/1996 | Weithmann et al. . |
| 5,744,664 | 4/1998 | Brekner et al. . |
| 5,747,664 | 5/1998 | Schleyerbach et al. . |

FOREIGN PATENT DOCUMENTS

| | | |
|---|---|---|
| 39 35 016 | 4/1991 | (DE) . |
| 43 10 964 | 10/1993 | (DE) . |
| 0 013 376 | 7/1980 | (EP) . |
| 0 217 206 | 4/1987 | (EP) . |
| 0257882 | 3/1988 | (EP) . |
| 0 538 783 A1 | 10/1992 | (EP) . |
| 0 527 736 | 2/1993 | (EP) . |
| 0607776 | 7/1994 | (EP) . |
| WO 91 17748 | 11/1991 | (WO) . |
| WO 9424095 | 10/1994 | (WO) . |
| WO 9632965 | 10/1996 | (WO) . |

OTHER PUBLICATIONS

G. Panayotou et al., "Riding the Evanescent Wave", Current Biology, vol. 3, No. 12, pp. 913–915, 1993.
Biacore 2000, "Surface Plasmon Resonance". (Jan. 2, 2000).
Kurtz et al., "Leflunomide: an active antiinflammatory and antiproliferative agent in models of dermatologic disease", Chemical Abstracts, vol. 123, No. 19, Nov. 6, 1995, p. 57.
Robertson et al., "Leflunomide: Inhibition of A–antigen induced autoimmune uveitis in Lewis rats", Chemical Abstracts, vol. 122, No. 5, Jan. 30, 1995, p. 68–69.
Thoss et al., "Immunomodulation of rat antigen–induced arthritis by leflunomide alone and in combination with cyclosporin", Chemical Abstracts, vol. 124, No. 19, May 6, 1996, p. 108.
Dias et al., "Measurement of the active leflunomide metaboite (A 77 1726) by reverse–phase high–performance liquid chromatopography", Chemical Abstracts, vol. 122, No. 15, Apr. 10, 1995, p. 9.

*Primary Examiner*—Floyd D. Higel
*Assistant Examiner*—Ebenezer Sackey
(74) *Attorney, Agent, or Firm*—Finnegan, Henderson, Farabow, Garrett, & Dunner, L.L.P.

(57) ABSTRACT

A compound of the formula

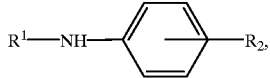

(I)

where $R^1$ is the radical of the formula II or III

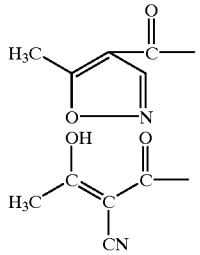

(II)

(III)

is suitable for the production of a pharmaceutical for the treatment of inflammations, carcinomatous diseases, or autoimmune diseases. A compound of the formula IV

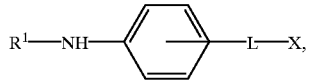

(IV)

is suitable for the production of specific antibodies against a compound of the formula I for the discovery of specific-binding proteins from cell extracts, serum, blood, or synovial fluids, for the purification of proteins, for the modification of microtiter plates, or for the preparation of chromatography material, in particular of affinity chromatography material, and for use in diagnostics.

8 Claims, No Drawings

ISOXAZOLE AND CROTONAMIDE DERIVATIVES AND THEIR USE AS PHARMACEUTICALS AND DIAGNOSTICS

This is a divisional of application Ser. No. 09/296,254, filed Apr. 22, 1999 now U.S. Pat. No. 6,121,479, which is a divisional of application Ser. No. 09/012,570, filed Jan. 23, 1998 now U.S. Pat. No. 5,977,151, all of which are incorporated herein by reference.

The invention relates to novel isoxazole and crotonamide derivatives, their preparation and use as pharmaceuticals, and their use as an antigen for the production of antibodies and their use in diagnosis and purification processes.

BACKGROUND OF THE INVENTION

Isoxazole and crotonamide derivatives having antiinflammatory, immunosuppressant, or antiproliferative action have been disclosed (EP 0 013 376; EP 0 217 206; EP 0 527 736). The analytical determination of these compounds in animal and human sera is possible with the aid of conventional chromatographic processes. The disadvantage of these chromatographic processes is a high outlay in terms of apparatus, complicated sample preparation steps and low sample throughput.

Immunological determination and analysis processes are a rapid and reliable alternative to chromatographic processes. The production of suitable antibodies is crucial for carrying out these alternative processes.

SUMMARY OF THE INVENTION

The invention aims, by modification of isoxazole and crotonamide derivatives, to make available compounds which are suitable for antibody production, can be coupled to polymers and can be employed as tracers in radioimmunoassays.

It has been found that compounds of the formula I are suitable for achieving this object where, on the aromatic ring of the aniline moiety, there are one or more functional groups which can be coupled covalently to polymers as such or via a spacer function.

The invention therefore relates to compounds of the formula I

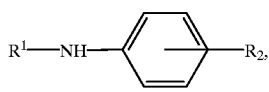

(I)

and/or a physiologically tolerable salt of the compound of the formula I and/or an optionally stereoisomeric form of the compound of the formula I, where $R^1$ is the radical of the formula II or III

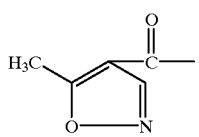

(II)

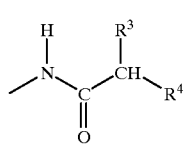

(III)

and $R^2$ is a) —O—$(CH_2)_n$—CH=$CH_2$, in which n is the integer 1, 2, or 3, b) —O—$(CH_2)_m$—$CH_2$-halogen, in which m is the integer 1, 2, or 3 and halogen is fluorine, chlorine, bromine, or iodine, c) the radical of the formula V

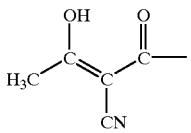

(V)

in which
$R^3$ is
1) halogen or
2) —$NH_2$ and
$R^4$ is
1) a hydrogen atom or
2) a radical of an amino acid, or d) —$NH_2$.

DETAILED EMBODIMENTS OF THE INVENTION

Preferred compounds of the formula I are those wherein $R^1$ is the radical of the formula II or III and
$R^2$ is a) —O—$(CH_2)_m$—$CH_2$-halogen, in which m is the integer 2 and halogen is bromine or iodine,
b) —O—$CH_2$—CH=$CH_2$ or
c) —NH—C(O)—CH($R^3$)($R^4$),
in which $R^3$ is bromine, —$NH_2$, or chlorine and $R^4$ is a hydrogen atom.

Particularly preferred compounds of the formula I are those such as 2-cyano-3-hydroxybut-2-enecarboxylic acid (4-allyloxyphenyl)amide,
2-cyano-3-hydroxybut-2-enecarboxylic acid (4-(3-iodopropoxy)phenyl)amide,
2-cyano-3-hydroxybut-2-enecarboxylic acid (4-(2-aminoacetylamino)phenyl)amide,
5-methylisoxazole-4-carboxylic acid (4-(2-aminoacetylamino)phenyl)amide,
2-cyano-3-hydroxybut-2-enecarboxylic acid (4-(2-bromoacetylamino)phenyl)amide, or
5-methylisoxazole-4-carboxylic acid (4-(2-bromoacetylamino)phenyl)amide.

The radical $R^2$ in formula I can be in the meta-, ortho-, or para-position relative to the "NH" group on the phenyl ring, preferably in the para-position.

The compounds of the formula I can optionally be present as optical isomers, diastereomers, racemates, or as mixtures thereof. The term "amino acid" is understood as meaning the stereoisomeric forms, e.g., D and L forms, of the following compounds: asparagine, valine, arginine, aspartic acid, glutamine, glutamic acid, tryptophan, β-alanine, lysine, proline, glycine, γ-aminobutyrate, Nε-acetyllysine, Nδ-acetylornithine, Nγ-acetyldiaminobutyrate, Nα-acetyidiaminobutyrate, histidine, isoleucine, leucine, methionine, phenylalanine, serine, cysteine, threonine, alanine, and tyrosine. L-Amino acids are preferred. The amino acid residue Gly is particularly preferred.

Amino acid residues are derived from the corresponding amino acids. The brief notation for the amino acids follows the generally customary notation. The radical ($R^4$) represents the side chain of the respective amino acid.

Suitable physiologically tolerable salts of the compounds of the formula I are, for example, alkali metal, alkaline earth metal and ammonium salts, including those of organic ammonium bases and salts of the protonated amino acid residues.

The invention also relates to a process for the preparation of a compound of the formula I and/or a physiologically tolerable salt of a compound of the formula I and/or an optionally stereoisomeric form of a compound of the formula I, which comprises:

a) reacting a compound of the formula VI

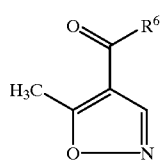

(VI)

where $R^6$ is the radical OH, Cl, or Br, with a compound of the formula VII

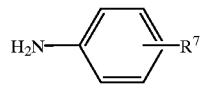

(VII)

where $R^7$ is
1) —$NH_2$,
2) an —NH—C(O)—$CH_2$—NH-protective group, for in which protective group is an amine protective group, for example Boc,
3) —NH—C(O)—$CH_2$-halogen or
4) —OH to give a compound of the formula I in which $R^1$ is the radical of the formula II and $R^2$ is —$NH_2$, —NH—C(O)—$CH_2$—NH-protective group, —OH, or —NH—C(O)—$CH_2$-halogen, or b) reacting a compound prepared by process a), in which $R^7$ is —OH, with an alkyl halide or a dihaloalkane in which the alkyl moiety has 2, 3, or 4 carbon atoms to give a corresponding compound of the formula I, or c) reacting a compound prepared by process a), in which $R^7$ is —OH, with an unsaturated alkyl halide in which the alkyl moiety has 3, 4, or 5 carbon atoms to give a corresponding compound of the formula I, or d) reacting a compound prepared by process a), in which $R^7$ is —$NH_2$, with a carboxylic acid halide such as bromoacetyl bromide to give a compound of the formula I in which $R^2$ is the radical of the formula V, $R^3$ is halogen and $R^4$ is a hydrogen atom, or e) reacting an aromatic diamine such as p-phenylenediamine with an amino acid protected on the amino group to give a compound of the formula VII in which $R^7$ is a radical of the formula V, $R^3$ is —$NH_2$ and $R^4$ is a protected amino acid and then reacting as in process a) to give a corresponding compound of the formula I, or f) removing the protective group in a compound of the formula I prepared by process a) or e), or g) converting a compound of the formula I prepared by processes a) through f), where $R^1$ is the radical of the formula II, into a compound of the formula I where $R^1$ is the radical of the formula III, or h) either isolating the compound of the formula I prepared by processes a) through g) in free form or, in the case of the presence of acidic or basic groups, optionally converting it into physiologically tolerable salts.

In the process step according to a), it is possible to convert, for example, an isoxazole-4-carboxylic acid ($R^6$ is —OH) into an acid chloride by methods known from the literature, e.g., by means of thionyl chloride or phosphorus oxychloride in an aprotic solvent (e.g., toluene, tetrahydrofuran (THF) or a chlorinated hydrocarbon) and then to react it with an aromatic amine which is optionally substituted in a suitable manner with addition of an organic base, e.g., with a tertiary amine (e.g., triethylamine or N-ethyimorpholine), in a dipolar aprotic solvent, for example THF or a chlorinated hydrocarbon. Alternatively, the amide formation can be carried out directly from the carboxylic acid with addition of a condensing reagent known from peptide chemistry, e.g., dicyclohexylcarbodiimide. The second variant is particularly suitable for aromatic amines having further amino or alcohol radicals.

In process steps b) or c), the hydroxyl group introduced by means of the aniline moiety is further functionalized by reacting this:

1) with an alkyl halide or a dihaloalkane such as 1,3-diiodopropane with addition of an organic or inorganic base, e.g., potassium carbonate, to give a correspondingly substituted araliphatic ether, where in the latter case dimerization can be avoided by an appropriately large excess of alkylating agent or use thereof as a solvent, such that in the product an alkyl halide function remains for the further coupling of the product to a stationary phase, or 2) reacting with an unsaturated alkyl halide, e.g., an allyl or propargyl halide, preferably allyl bromide, in a dipolar aprotic solvent, such as tetrahydrofuran (THF), acetone or chlorinated hydrocarbons under similar conditions to an allyl or propargyl ether, where when using acetone as a solvent and potassium carbonate as a base simultaneously the ring opening of the isoxazole moiety (radical of the formula II) described under g) occurs.

In process step d), the amino group is reacted with a carboxylic acid halide, e.g., bromoacetyl bromide, with addition of an organic base such as a tertiary aromatic amine (e.g., triethylamine or N-ethylmorpholine) in a dipolar aprotic solvent such as THF or a chlorinated hydrocarbon.

In process step e), an aromatic diamine, e.g., p-phenylenediamine, is converted into the monoamide in a controlled manner using an amino acid protected on the amino group, e.g., N-Boc-glycine, using a condensing agent, e.g., dicyclohexylcarbodiimide, then the anilide formation is carried out as described under process step a), and finally the amine protective group carried along is removed under standard conditions known from peptide chemistry (process step f)).

In process step g), a compound prepared under a) through f) is subjected to a base-induced ring opening of the isoxazole moiety, the reaction preferably being carried out in an aqueous/organic solvent mixture, e.g., THF/water or ethanol/water, using an excess of an organic or inorganic base, e.g., NaOH, ammonia solution, or potassium carbonate.

Provided the compounds of the general formula I occur in diastereoisomeric or enantiomeric forms and are obtained in the selected synthesis as mixtures thereof, separation into the pure stereoisomers is carried out either by chromatography on an optionally chiral support material, or provided the racemic compounds of the formula I are capable of salt formation, by fractional crystallization of the diastereomeric salts formed with an optically active base or acid as auxiliary. In a manner which is identical in principle, the racemic compounds of the formula I which contain a basic group such as an amino group can be converted into the pure enantiomers using optically active acids such as (+)-camphor-10-sulfonic acid, D- and L-tartaric acid, D- and L-lactic acid or (+) and (−)-mandelic acid.

The invention also relates to pharmaceuticals which contain an efficacious amount of at least one compound of the formula I and/or a stereoisomeric form of the compound of the formula I and/or a physiologically tolerable salt of the compound of the formula I, in addition to pharmaceutically suitable and physiologically tolerable excipients, additives and/or active compounds and auxiliaries. The pharmaceuticals according to the invention can be administered intravenously, parenterally, topically, rectally, or orally.

The pharmaceuticals according to the invention are preferably suitable for the prophylaxis and/or therapy of carcinomatous diseases, inflammations, and autoimmune diseases.

These include, for example, rheumatic diseases, acute, and chronic inflammations of muscles, joints, or of the gastrointestinal tract, allergic airway diseases, psoriasis, or autoimmune diseases, e.g., systemic lupus erythematosus ("SLE"), type II diabetes, myasthenia gravis, Sjögren syndrome, dermatomyositis, sclerodermatitis, or multiple sclerosis ("MS"). The carcinomatous diseases include, for example, lung cancer, leukemia, Kaposi's sarcoma, ovarian cancer, sarcoma, meningioma, intestinal cancer, cancer of the lymph nodes, brain tumors, breast cancer, stomach cancer, cancer of the pancreas, cancer of the prostate, or skin cancer.

The invention also relates to a process for the production of a pharmaceutical according to the invention, which comprises bringing at least one compound of the formula I into a suitable administration form using a pharmaceutically suitable and physiologically tolerable excipient and, if appropriate, further suitable active compounds, additives, or auxiliaries.

Suitable solid or liquid pharmaceutical preparation forms are, for example, granules, powders, coated tablets, tablets, (micro)capsules, suppositories, syrups, juices, suspensions, emulsions, drops, or injectable solutions, and preparations having protracted release of active compound, in whose preparation customary auxiliaries, such as excipients, disintegrants, binders, coating agents, swelling agents, glidants, or lubricants, flavorings, sweeteners, and solubilizers are used. Frequently used auxiliaries which may be mentioned are, for example, talc, starch, magnesium carbonate, titanium dioxide, lactose, mannitol and other sugars, lactoprotein, gelatin, cellulose and its derivatives, animal and vegetable oils such as cod liver oil, sunflower, groundnut, or sesame oil, polyethylene glycols, and solvents, such as, for example, sterile water and mono- or polyhydric alcohols, e.g., glycerol.

The pharmaceutical preparations are preferably prepared and administered in dose units, each unit containing as active constituent a certain dose of the compound of the formula I according to the invention. In the case of solid dose units such as tablets, capsules, coated tablets, or suppositories, this dose can be up to approximately 1000 mg, but preferably approximately 50 to 300 mg, and in the case of injection solutions in ampule form up to approximately 300 mg, but preferably approximately 10 to 100 mg. For the treatment of an adult patient approximately 70 kg in weight, depending on the efficacy of the compound of the formula I, in the case of humans and animals, daily doses of approximately 50 to 3000 mg of active compound are preferred. In the case of oral administration, approximately 150 to 1000 mg is preferred and, in the case of intravenous administration, approximately 50 to 1000 mg is preferred, more preferably, approximately 100 to 300 mg. Under certain circumstances, however, higher or lower daily doses may also be appropriate. The daily dose can be administered either by single administration in the form of an individual dose unit or else of several smaller dose units or by multiple administration of subdivided doses at specific intervals.

The invention further relates to a compound of the formula I which is optionally coupled to polymers or solids via bridging members. These are compounds of the formula IV

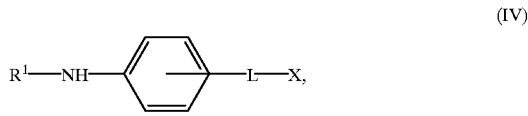

(IV)

where $R^1$ is the radical of the formula II or III

(II)

(III)

is a bridging member from the group
 a) —O—,
 b) —$NR^5$—, in which $R^5$ is a hydrogen atom,
 c) —O—$(CH_2)_n$—$CH_2$—, in which n is the integer 1, 2, or 3, d) —NH—C(O)—CH($R^4$)—$R^3$, in which $R^3$ is
   a) a covalent bond or
   b) —NH— and
  $R^4$ is
   a) a hydrogen atom or
   b) a radical of an amino acid, or
 e) a bridging member L, defined as under a) to d), which has a spacer, in which the spacer is a radical of the group
  1) —NH—$(CH_2)_m$—S—, in which m is an integer from 1 to 12, and X is a polymer or solid.
The radical "L—X" in the formula IV can be in the meta-, ortho-, or para-position relative to the "NH" group on the phenyl ring, preferably in the para-position. The term "polymer" is understood as meaning, for example, synthetic or natural polymers from the group consisting of polystyrene, polypropylene, polyvinyl chloride, latex, polysaccharides, Sepharose, proteins, lipids, silicates, or nucleic acids. The polymers optionally have to be provided with one or more functional radicals from the group consisting of —OH, —COOH, —NH$_2$ and —CO— in order that they can be coupled to the compounds of the formula I. General methods for the coupling of the compounds of the formula I to solids are described, for example, in BI Application Handbook, Ed. 1994, FIG. 4.1, (Merck AB, Uppsala, Sweden). The term "solid" represents insoluble bodies which can be particulates or can occur in geometric embodiments such as tubes, beads, or microtiter plates.

Preferred compounds of the formula IV are those where a compound of the formula I is coupled to a solid or a polymer. Particularly preferred compounds of the formula IV are those where a compound of the formula I such as 5-methylisoxazole4-carboxylic acid (4-(2-bromoacetylamino)phenyl)amide or 2-cyano-3-hydroxybut-2-enecarboxylic acid (4-(2-bromoacetylamino)phenyl) amide is coupled to a solid or a polymer.

The compounds of the formula IV are also suitable for the discovery of specific binding proteins from cell extracts, serum, blood, or synovial fluids, for the purification of proteins, for the modification of microtiter plates or for the preparation of chromatography material, in particular of affinity chromatography material. The proteins suitable for purification are in direct interaction with the compounds of the formula I bound to the polymer or solid. The compounds are also suitable for use in diagnostics.

A particularly suitable solid in the case of the compounds of the formula IV is a BIAcore® CM5 chip or a stationary phase for chromatographic investigations or separations, and also microtiter plates.

EXAMPLE 1

5-Methylisoxazole4-carboxylic acid (4-(2-bromoacetylamino)phenyl)amide

Stage a)

5-Methylisoxazole-4-carboxylic acid (4-aminophenyl)amide 10.1 g (0.08 mol) of 5-methylisoxazole-4-carboxylic acid and 8.65 g (0.08 mol) of p-phenylenediamine are dissolved in 300 ml of tetrahydrofuran and 18.05 g (0.088 mol) of dicyclohexylcarbodiimide are added. After 5 hours ("h"), the deposited precipitate is filtered off with suction, the organic phase is concentrated and the product is chromatographed on silica gel by means of ethyl acetate/petroleum ether with addition of 1% glacial acetic acid and then crystallized from ethyl acetate/petroleum ether. The yield of the process was 6.8 g of acetate salt with a melting point of 123° C. to 128° C.

Stage b)

5-Methylisoxazole-4-carboxylic acid (4-(2-bromoacetylamino)phenyl)amide 2.17 g (0.01 mol) of the product from stage a) are initially introduced into 50 ml of tetrahydrofuran together with 1.9 g (0.016 mol) of N-ethylmorpholine and, in an ice bath, a solution of 2.4 g (0.012 mol) of bromoacetyl bromide is added dropwise and the mixture is then additionally stirred at room temperature for 5 h. After addition of 5 ml of water, it is acidified to pH 2 using 1 N HCl, the product is extracted with ethyl acetate, and the organic phase is washed with water, dried and concentrated. The product is crystallized from ethyl acetate/petroleum ether. The yield of the process was 2.0 g with a melting point of 179° C.

The resulting product has an $^1$H-NMR: (DMSO-d$_6$): 2.7 (s, 3H), 4.05 (s, 2H), 7.5–7.75 (m, 4H), 9.1 (s, 1H), 10.1 and 10,45 (in each case sb, 1H).

EXAMPLE 2

2-Cyano-3-hydroxybut-2-enecarboxylic acid (4-(2-bromoacetylamino)phenyl)amide 0.5 g (0.0015 mol) of the product from Example 1 is dissolved in 10 ml of tetrahydrofuran and 2 ml of 1N aqueous NaOH is added with ice-cooling. The reaction is monitored by TLC and after completion (approximately after 60–90 min) the product is precipitated by acidification with 2.25 ml of 1N aqueous hydrochloric acid and addition of 100 ml of water, filtered, washed with water, then washed with a little ethyl acetate with stirring and dried under reduced pressure. The yield of the process was 0.28 g with a melting point greater than 210° C.

The resulting product has an $^1$H-NMR: (DMSO-d$_6$): 2.28 (s, 3H), 4.04 (s, 2H), 7.4–7.7 (m, 4H), 8.5–10 (sb, 1H), 10.4 (sb, 2H).

EXAMPLE 3

5-Methylisoxazole-4-carboxylic acid (4-(2-aminoacetylamino)phenyl)amide-hydrochloride Stage a)

2-tertiary-Butoxycarbonylaminoacetylamino-p-phenylenediamine 8.65 g (0.08 mol) of p-phenylenediamine are dissolved in 300 ml of absolute tetrahydrofuran (THF) together with 15.3 g (0.088 mol) of N-Boc-glycine, and 18.05g (0.088 mol) of dicyclohexylcarbodiimide is added in portions. After 5 h, the deposited precipitate is filtered off with suction, the filtrate is concentrated, and the product is purified by chromatography on silica gel by means of ethyl acetate/methanol/acetic acid and then crystallized from ethyl acetate/petroleum ether. The yield of the process was 13.5 g with a melting point 144° C.

Stage b)

5-Methylisoxazole-4-carbonyl chloride 127.1 g (1.0 mol) of 5-methylisoxazole-4-carboxylic acid are initially introduced into 1 l of toluene, 129.8 g (1.1 mol) of thionyl chloride are added dropwise and the mixture is then heated at 80° C. for 6 h. The volume is concentrated under reduced pressure to approximately one half and the toluene solution is used directly for further reactions.

Stage c)

5-Methylisoxazole-4-carboxylic acid (4-(2-tertiarybutoxycarbonyl aminoacetylamino)phenyl) amide 13.5 g (0.05 mol) of the product from stage a) are initially introduced into 100 ml of THF together with 7.6 ml (0.06 mol) of N-ethylmorpholine and 30 ml of the solution from stage b) (corresponds to 0.06 mol) are added dropwise at 0° C. The mixture is stirred at room temperature for a further 5 h, hydrolyzed with aqueous citric acid, and the product is extracted with ethyl acetate, washed with water, dried over sodium sulfate and concentrated under reduced pressure. The yield of the process was 12 g with a melting point of 139° C.

Stage d)

5-Methylisoxazole-4-carboxylic acid (4-(2-amino-acetylamino)phenyl)amide hydrochloride 6 g (0.017 mol) of the product from stage c) are dissolved in 180 ml of dichloromethane and 18 ml of trifluoroacetic acid are added. The mixture is stirred at room temperature for 1 h and concentrated, and the product is converted into the hydrochloride by dissolving it in ethanol, adding an excess of ethanolic HCl, concentrating and washing the residue by stirring with ethyl acetate. The yield of the process was 2.5 g with a melting point of 210° C.

The resulting product has an $^1$H-NMR: (DMSO-$d_6$): 2.7 (s, 3H), 3.7–3.9 (m, 2H), 7.6 and 7.72 (in each case 2H, AA'BB'), 8.25 (sb, 2H), 9.3, 10.2 and 10.75 (in each case s, 1H)

EXAMPLE 4

2-Cyano-3-hydroxybut-2-enecarboxylic acid (4-(2-aminoacetylamino)phenyl)amide trifluoroacetate 6 g (0.017 mol) of the product from Example 3, stage c) are dissolved in 20 ml of 1N sodium hydroxide solution/2 ml ethanol and the mixture is stirred at room temperature until ring opening is complete (approximately 3 h). On acidifying with aqueous citric acid, the Boc-protected product is obtained in solid form and is filtered on a suction filter and dried (melting point 189° C., yield 5.5 g). 5 g of this intermediate product are treated with trifluoroacetic acid in dichloromethane analogously to Example 3d) and the product is crystallized from ethanol as the trifluoroacetate by means of ethyl acetate and petroleum ether. The yield of the process was 5.0 g with a melting point of 209° C.

The resulting product has an $^1$H-NMR (DMSO-$d_6$): 2.15 (s, 3H), 3.7–3.85 (m, 2H), 7.49 (s, 4H), 8.1 (sb, 3H), 10.3 and 11.2 (in each case sb, 1H).

EXAMPLE 5

2-Cyano-3-hydroxybut-2-enecarboxylic acid (4-(3-iodopropoxy)phenyl)amide

Stage a)

5-Methylisoxazole-4-carboxylic acid (4-(3-iodopropoxy)phenyl)amide 6.5 g (0.03 mol) of 5-methylisoxazole-4-carboxylic acid (4-hydroxyphenyl)amide are dissolved in 57 ml (0.5 mol) of 1,3-diiodopropane and 26.2 g (0.19 mol) of finely ground potassium carbonate are added with intensive stirring. The reaction is complete after approximately 4 h. Working up is carried out by means of filtration, concentration and chromatography on silica gel by means of ethyl acetate/petroleum ether 1:1 with addition of 1% glacial acetic acid. The yield of the process was 6.7 g.

Stage b)

2-Cyano-3-hydroxybut-2-enecarboxylic acid (4-(3-iodopropoxy)phenyl)amide 5.5 g of the product from stage a) are treated in 200 ml of an approximately 1N methanolic ammonia solution until ring opening is complete, the mixture is concentrated, the residue is taken up with dilute acetic acid and chromatographed by means of ethyl acetate/petroleum ether with addition of 1% glacial acetic acid, then crystallized from ethyl acetate/petroleum ether. The yield of the process was 2.3 g with a melting point of 149° C.

The resulting product has an $^1$H-NMR (DMSO-$d_6$): 2.1–2.4 (m, 2H and s, 3H at 2.3 ppm), 3.4 and 4.02 (in each case t, 2H), 6.92 and 7.42 (in each case 2H, AA'BB'), 7.2–8.5 (ssb, 1H), 10.2 (s, 1H).

EXAMPLE 6

2-Cyano-3-hydroxybut-2-enecarboxylic acid (4-allyloxyphenyl)amide 1.5 g (0.0068 mol) of 5-methylisoxazole-4-carboxylic acid (4-hydroxyphenyl)amide are dissolved in acetone, 5.8 ml (0.068 mol) of allyl bromide and, under intensive stirring, 9.3 g (0.068 mol) of finely ground potassium carbonate are added, then the mixture is stirred overnight at room temperature. It is filtered, the filtrate is concentrated, and the residue is taken up in water and recrystallized from ethyl acetate/petroleum ether. The yield of the process was 8.0 g with a melting point of 162° C. to 164° C.

The resulting product has an $^1$H-NMR (DMSO-$_6$): 2.3 (s, 3H), 4.45–4.63 (m, 2H), 5.15–5.38 (m, 2H), 5.9–6.2 (m, 1H), 6.95 and 7.42 (in each case 2H, AA'BB'), 10.0 (sb, 1H), 12.5–14.5 (ssb, 1H).

Pharmacological Tests

The cell culture in vitro proliferation test is used as an activity test for the compounds of the formula I.

EXAMPLE 7

Proliferation Test

Clicks/RPMI 1640 medium (50:50) with L-glutamine and without NaHCO$_3$ in powder form for 10 l (Seromed, Biochrom, Berlin, FRG), is dissolved in 9 l of double-distilled water and sterile-filtered into bottles each containing 900 ml.

Wash Medium 900 ml of base medium are buffered with 9.5 ml of 7.5% strength sodium hydrogencarbonate solution and 5 ml of HEPES (N-2-hydroxyethylpiperazine-N-2-ethanesulfonic acid) (Gibco, Eggenstein, FRG).

Use Medium 900 ml of base medium plus 19 ml of NaHCO$_3$ solution (7.5%; 10 ml of HEPES solution and 10 ml of L-glutamine solution (200 mM)). The medium used for mitogen-induced lymphocyte proliferation is use medium which is enriched with 1% heat-inactivated (30 min, 56° C.) fetal calf serum (FCS).

Tumor Cell Medium

For keeping tumor cells and hybridoma cells, use medium containing 5% FCS is prepared.

Culture Medium for Cell Lines

For keeping cell lines, 900 ml of use medium containing 10% FCS, 10 ml of NEA (non-essential amino acids) solution (Gibco), 10 ml of sodium pyruvate solution (100 mM, Gibco) and 5 ml of 10$^{-2}$ M mercaptoethanol are mixed.

Isolation and Processing of the Spleen Cells for Mitogen-induced Lymphocyte Proliferation The mice are killed by cervical dislocation and the spleens are removed under sterile conditions. The spleens are cut up on a sterile sieve having a mesh width of 80 mesh and, using the plunger of a plastic syringe (10 ml), carefully strained into a Petri dish containing use medium. To remove the erythrocytes from the spleen cell suspension, the mixture is incubated at room temperature for approximately 1 min, with occasional shaking in hypotonic, 0.17 M ammonium chloride solution. The erythrocytes are lyzed in the course of this, while the vitality and reactivity of the lymphocytes is not affected. After centrifugation (7 min/340 g), the lysate is discarded, and the cells are washed twice and then taken up in the respective test medium.

Mitogen-induced Lymphocyte Proliferation $5 \times 10^5$ processed spleen cells from female NMRI mice are pipetted together with various mitogens and preparation (compound of the formula I) into 200 $\mu$l of test medium per hollow in flat-bottom microtiter plates. The following mitogen and preparation concentrations are used:

Concanavalin A [Serva]: 0.5–0.25–0.12 $\mu$g/ml

Lipopolysaccharide [Calbiochem]: 1.0–0.5–0.1 $\mu$g/ml

Phytohemagglutinin [Gibco]: 0.5–0.25–0.12% stock solution

Pokeweed mitogen [Gibco] compound 1 or 2: 50, 25, 10, 7.5, 5, 2.5, 1, 0.5, 0.1 $\mu$mol.

The positive controls are defined as the group with mitogen additions and without preparation. The negative controls are cells in culture medium with preparation and without mitogen additions. Each mitogen concentration is tested four times with all preparation concentrations. After incubation at 37° C./5% $CO_2$ for 48 h, 25 $\mu$l/hollow of tritium-thymidine (Amersham) having an activity of 0.25 $\mu$Ci/hollow (9.25×10$^3$ Bq) is added to the cells. A further incubation under the same conditions for a period of 16 h follows. To evaluate the test batch, the cells are harvested on filter paper by means of a cell harvester (Flow Laboratories), nonincorporated thymidine being collected in a separate waste bottle. The filter paper is dried, punched out and added to scintillation containers together with 2 ml of scintillator (ROTISZINT 22, Roth), which are then cooled at 4° C. for a further 2 h. The amount of the radioactivity incorporated by the cells is measured in a beta-counter (Packard, TriCARB-460c).

Preparation of the Tumor Cells and Cell Lines for the Proliferation Test

The tumor cells or cell lines used in the test are taken from the stock solution in the logarithmic growth phase, washed twice with wash medium and suspended in the appropriate medium.

Carrying-out and Evaluation of the Proliferation Tests

The proliferation test is carried out in round-bottom microtiter plates. Compounds of the formula I and interleukins are dissolved in 50 $\mu$l each/hollow of the appropriate medium and the cell count ($5 \times 10^5$) is adjusted with 100 $\mu$l/hollow so that a final volume of 200 $\mu$l/hollow results. In all tests, the values are determined four times. Cells without preparations and without growth factor are defined as a negative control and cells without preparation with growth factor afford the values for the positive control. The value of the negative control is subtracted from all values determined and the difference of positive control minus negative control is set at 100%.

The microtiter plates are incubated at 37° C./5% $CO_2$ for 72 h and the proliferation rate is determined correspondingly as in mitogen-induced lymphocyte proliferation. The cell lines were obtained from the strain collection, American Type Culture Collection ("ATCC").

TABLE 1 shows the concentrations at which a 50% inhibition occurs:

| Compound of the formula I according to Example | Cell line | | |
| --- | --- | --- | --- |
| | A20.2.J ($\mu$M) | EL 4 ($\mu$M) | K562 ($\mu$M) |
| 1 | 0.8 | 0.8 | 50 |
| 2 | 15.0 | 6.0 | 20 |
| 5 | 50.0 | 25.0 | not determined |

EXAMPLE 8

Process for the Binding of the Compound According to Example 2 to the BIAcore® CM5 Matrix The starting material is a CM5 chip from Pharmacia Biosensor having a carboxymethyldextran surface (BIApplication Handbook, Ed. 1994, Merck AB, Uppsala, Sweden). The coupling steps are all carried out at a flow rate of 5 $\mu$l/min. All steps are carried out at 25° C. using Hepes buffered saline ("HBS") pH 7.4 as the running buffer.

1st step: 35 $\mu$l of a 1:1 mixture of 0.05 M NHS (N-hydroxysuccinimide) and 0.2 M EDC (N-ethyl-N'-(dimethylaminopropyl)carbodiimide) in order to activate the chip surface.

2nd step: 35 $\mu$l of a 40 mM cystamine dihydrochloride solution in 0.1 M sodium borate buffer pH 8.5.

3rd step: 35 $\mu$l of ethanolamine hydrochloride pH 8.5 to saturate unoccupied matrix structures.

4th step: 35 $\mu$l of 0.1 M dithiothreitol in 0.1 M sodium borate buffer pH 8.5.

5th step: 35 $\mu$l of a solution containing compound according to Example 2 (10 mg/ml) in 0.1 M sodium borate buffer pH 7.5.

EXAMPLE 9

BIAcore® Method Used for the Analyses

The analysis was carried out essentially as described in Current Biology, Vol. 3, No. 12, pages 913–915 (1993).

System: BIAcore® 2000 with corresponding software, Pharmacia Biosensor AB, Uppsala, Sweden Chip: CM5 sensor chip, Pharmacia Biosensor AB Coating: according to Example 8

Running buffer: HBS buffer, BIA certified, Pharmacia Biosensor AB

Flow rate: 10 $\mu$l/min

Injection: 5 min association phase per 50 $\mu$l of the sample to be analyzed.

Rinsing time: 180 sec 3 min dissociation phase

Regeneration: 2×15 sec using 0.05% sodium dodecylsulfate

A) Binding of Various Serum Albumins

| Type | Resonance Units |
| --- | --- |
| Bovine | 50 |
| Human | 294 |
| Rat | 1061 |
| Mouse | 151 |
| Chicken | 8 |
| Donkey | 480 |
| Sheep | 331 |

The term "Resonance Units" is a quantitative unit which is proportional to the amount of protein bound.

B) Binding of Various Dehydrogenases

| Enzyme | Resonance Units |
| --- | --- |
| Glyceraldehyde phosphate DH (25 nM) | 69 |
| Glyceraldehyde phosphate DH (50 nM) | 148 |
| Glyceraldehyde phosphate DH (100 nM) | 297 |
| Glyceraldehyde phosphate DH (250 nM) | 603 |
| Dihydroorotate DH (50 nM) | 203 |
| Dihydroorotate DH (100 nM) | 425 |
| Dihydroorotate DH (250 nM) | 1064 |
| Pyruvate kinase DH (50 nM) | 85 |
| Pyruvate kinase DH (100 nM) | 189 |
| Pyruvate kinase DH (250 nM) | 505 |

DH represents the enzyme designation dehydrogenase

The relative binding strengths of the dehydrogenases investigated were compared with one another at a defined protein concentration. At a protein concentration of 1 µM, the binding of the dihydroorotate DH was the strongest, followed by lactate DH, glyceraldehyde phosphate DH and pyruvate kinase.

EXAMPLE 10

Affinity Chromatography

The compound according to Example 1 is coupled to a support matrix via its reactive bromine group. The support material employed is FRACTOGEL® EMD-SH (Merck KGaA, Darmstadt). The covalent bonding is carried out according to a standard protocol as specified in DE 43 10 964. The gel obtained is packed into a SUPERFORMANCE® (1 cm×5 cm) column (Merck KGaA) and connected to a high-pressure liquid chromatography unit (HPLC).

Isolation and Characterization of the Soluble Cell Proteins

The strain RAW 264.7 (ATCC strain collection) is cultured for 48 h until reaching confluence and washed free of the culture medium three times with cold, 4° C. PBS buffer, and the cells are transferred to PBS buffer and centrifuged at 200 g for 10 min. The cell processing is carried out at 4°C. The cell pellet is resuspended in buffer A consisting of 20 mM TRIS base, 2 mM $MgCl_2 \times 6\ H_2O$ and 1 mM dithiothreitol ("DTT"). A mixture of various protease inhibitors is added in order to prevent proteolysis by cell-endogenous proteases. The mixture is then homogenized in a glass potter. The suspension is then centrifuged at 22,000 g for 30 min at 4° C. to obtain the soluble proteins.

The supernatant is immediately reused for affinity chromatography. An aliquot of the supernatant is retained as a reference and the remainder is pumped onto the affinity column.

HPLC

An apparatus from Kontron Instruments, Milan, Italy is employed for affinity chromatography. The system consists of the components Autosampler 465, HPLC pump 422 and 422S, a high-pressure mixing valve M800, a Besta motor valve and a diode array detector 440. The data recording and analysis are carried out using the Data System 450-MT2/DAD series. The cell supernatant is diluted to a volume of 30 ml with water and injected at a flow rate of 1 ml/min. The breakthrough is collected and stored at 4° C., just as the fractions up to the completion of the chromatography.

The following buffers are used for the gradient elution of the proteins:

Composition of the PBS buffer:

NaCl 8.00 g/l
KCl 0.20 g/l
$KH_2PO_4$ 0.20 g/l
$Na_2HPO_4 \times 7H_2O$ 2.16 g/l Composition of the buffers used in Table 2:

Buffer: Composition:
1 PBS
2 PBS+0.5 M NaCl
3 PBS+150 mM A 77 1726b (sodium salt of N-(4-trifluoromethylphenyl)-2-cyano-3-hydroxycrotonamide)
4 $H_2O$
5 6 M urea
6 60% acetonitrile+0,1% trifluoroacetic acid (TFA)

After injecting the protein solution, the gradient according to Table 2 is started at a flow rate of 3 ml/min.

TABLE 2

| Time [min] | Gradient | Fraction |
| --- | --- | --- |
| 0–10 | $H_2O$ (4) | 1 |
| 10–15 | Gradient to PBS (1) | 2 |
| 15–20 | PBS (1) | |
| 20–35 | Gradient to PBS + 0.5 M NaCl (2) | 3 |
| 35–40 | PBS + 0.5 M NaCl (2) | |
| 40–50 | Gradient to PBS (2) | |
| 50–55 | PBS (1) | 4 |
| 55–70 | Gradient to PBS + preparation (3) | 5 |
| 70–75 | PBS + preparation (3) | |
| 75–90 | $H_2O$ (4) | 6 |
| 90–100 | Urea (5) | 7 |
| 100–110 | $H_2O$ (4) | 8 |
| 110–120 | Acetonitrile (6) | 9 |

The numbers in parentheses relate to the buffer used.

The fractions are collected, dialyzed against $H_2O$ at 4° C. for 48 h (exclusion limit of the dialysis membrane used 6000–8000 Da) (apart from acetonitrile fraction) and then lyophilized.

Protein Determination

After the lyophilization, the proteins are dissolved in 1 ml of 1% sodium dodecylsulfate ("SDS") and diluted to 0.5% SDS with water. Aliquots of this solution are taken and employed for the protein determination using the BCA test (Pierce). The proteins are evaporated (UNIVASPO 150H, UniEquip Power Heater, Martinsried, Germany) and then taken up in a suitable volume of sample buffer, consisting of 10 g of sucrose, 9 ml of 0.25 M TRIS/1M glycine solution, 7.8 ml of 10% SDS, 2.5 ml of Bromophenol Blue (0.1%), 4 ml of β-mercaptoethanol and 1.7 ml of water.

SDS-Page

For the preparation of an SDS gel having a polyacrylamide gradient of 10–17%, the following solutions of A and B are prepared:

| A | B |
| --- | --- |
| 5 ml of acrylamide (30%, 0.5%) | 8.5 ml of acrylamide (30%, 0.5%) |
| 3.75 ml of TRIS (3 M, pH 8.8) | 3.75 ml of TRIS (3 M, pH 8.8) |
| 6312 ml of water | 3.275 ml of glycerol |
| 0.15 m of SDS | 0.15 ml of SDS |

The polymerization is started by addition of 100 µl of 10% APS and 12.5 µl of TEMED. The collecting gel is prepared from 3 ml of acrylamide (10%, 0.5%), 1.36 ml of water, 1.45 ml of 0.5 M TRIS (pH 6.8), 60 µl of 10% SDS, 106 µl of 10% APS and 9 µl of TEMED. For the preparation of the analytical gels, approximately 10 µg of protein per track are loaded, for preparative gels 100 µg. The determination of the molecular weight is carried out by comparison with protein standard mixtures.

Sequencing

Protein fractions which show bands of concentrated proteins in the analytical gel are separated on a preparative scale and the separated proteins are immobilized by blotting on a PVDF membrane (Millipore). The proteins are visualized by staining with Coomassie and then subjected directly to Edman degradation. Proteins whose N-terminus is blocked are carefully cut out after electrophoresis on Coomassie-stained gels and washed with water until neutral. The small pieces of gel are pressed by two steel sieves lying one behind the other and having a mesh width of 100 μm and 32 μm and thus homogenized. The ointment-like material is dried to a low residual moisture in the UNIVAPO 150 H (UniEquip Power Heater, Martinsried, Germany). The proteins thus obtained are cleaved to peptides by incubation at 37° C. for 7 h with the enzyme endoproteinase LysdC (Boehringer Mannheim) (enzyme to protein ratio approximately 1:10) in a buffer consisting of 25 mM TRIS HCl, pH 8.5 and 1 mM EDTA.

The peptides obtained are eluted twice at 37° C. for 4 h using 1 ml each of 60% acetonitrile, 0.1% TFA. The combined eluates are evaporated in the UNIVAPO, and the peptides obtained are separated by reversed-phase chromatography. The chromatography is carried out on a LiChroCART® 125-2 SUPERSPHER® 60 column using a linear gradient (1%/min) of A: 0.1% TFA in $H_2O$ to B: 0.1% TFA in acetonitrile in 70 min.

The amino acid sequence of the purified peptides is carried out according to the Edman degradation principle on a 477 A gas-phase sequencer (Applied Biosystems). The identification of the PTH-AA is carried out on a 120A phenylthiohydantoin amino acid analyzer (Applied Biosystems) at 269 nm.

Western Blot Analysis

After the transfer of proteins from an SDS gel to the PVDF membrane, the uncoated area is blocked by incubation for 2 h with 2.5% chicken albumin (Sigma) in TBS, consisting of 45 g of NaCl, 30.3 g of TRIS base in 5 l, pH 7.4.

The first antibody is diluted in a suitable ratio with blocking buffer and incubated for 1 h. The blot is then washed three times for 5 min with TBS and 0.1% TWEEN 20 and incubated for 1 h with the second, POD-labeled antibody. The washing process is repeated and the bound antibody is visualized by means of a solution of 60 mg of 4-chloro-1-naphthol, 20 ml of methanol, 100 ml of TBS and 200 μl of hydrogen peroxide (30%).

It was possible to identify the proteins which were obtained in the NaCl (fraction 3) and A771726b (fraction 5) as set forth in Table 2, by means of 7 to 14 amino acid-long peptides. In the case of the 22 kDa protein, the determined amino acid sequence could be assigned to two proteins, MSP23 and NKEF-A. The reason for this lies in the high sequence homology of the two proteins of 93%. The sequencing results of the affinity chromatography were summarized in Table 3.

TABLE 3

| Fraction | Protein | Amino acid sequence | MW [Da] |
|---|---|---|---|
| NaCl (3) | Lactate DH M chain (LDH-A) | SADTLWGIQK | 36498 |
| | Cyclophilin A | TAENFRALSTGEK | 17971 |
| A 77 1726 B (5) | HSP90-β (HSP84) | EQVANSAFVERVRK | 83185 |
| | HSP70 (HSC73) | EIAEAYLGK | 70871 |
| | Pyruvate kinase $M_2$ | GPEIRTGLIK | 57755 |
| | EF1-α | STTTGHLIYK | 50164 |
| | Actin (γ-chain) | EITALAPSTMKRGILTLK | 41876 |
| | GAPDH | VIPELNGK | 35679 |
| | Malate DH | ITPFEEKVVE-FV | 35596 |
| | Lactate DH | NLRRVHP | 36367 |
| | Phosphoglyceratemutase | PMQFLGDEETVRK | 28635 |
| | MSP23/ NKEF-A | ATAVMPDGQFK | 22176 |

In the first column, the fraction number according to Table 2 is in parentheses.

Description of the Identified Proteins

The 18 kDa protein concentrated in fraction (3) was identified as Cyclophilin A. Cyclophilin A belongs to the large family of peptidylpropyl cis/trans isomerases which are involved in the mechanism of action of a number of immunosuppressant preparations, e.g., Cyclosporin A.

Lactate dehydrogenase, an enzyme of anaerobic glycolysis which catalyzes the reaction of pyruvate to lactate, was additionally identified in fraction (3). Lactate dehydrogenase occurs in animal tissue in at least five different isoenzyme forms. The isoenzyme prevalent in skeletal muscle contains four A chains, that dominant in the heart four B chains. In the present case, a peptide from the A chain of lactate dehydrogenase was identified.

Two proteins which belong to the heat shock proteins family were identified in fraction (5). The heat shock protein HSP70 dominant in eukaryotes is a member of a multigene family. The heat shock protein HSP90 is a cytosolic protein which is constitutively expressed even under normal conditions. It consists of two separate gene products, HSP84 and HSP86, which mutually have a sequence homology of 86%. It is known of HSP90 that it forms a complex with steroid hormone receptors and in this manner intervenes in the transcription of certain genes.

In fraction (5), three proteins of glycolysis were additionally found with glyceraldehyde-3-phosphate dehydrogenase ("GAPDH"), pyruvate kinase $M_2$ and phosphoglycerate mutase. These three enzymes derive from the lower phase of glycolysis and are present under native conditions in a multienzyme complex.

A band which was also concentrated very strongly in fraction (5) was identified as the elongation factor ("EF-1α"). EF-1α is an important eukaryotic translation factor. It is comparable in its function with the prokaryotic elongation factor EF-Tu and during protein biosynthesis in a GTP-dependent process transports aminoacyl-tRNAs from the cytosol to their acceptor sites on the ribosome.

It was additionally possible to detect actin in fraction (5). Actin is a protein occurring almost everywhere and in large amounts in eukaryotes. It is the main constituent of the musculature and of the cytoskeleton. The actin multigene family codes for at least four muscle actin forms and also for two cytoplasmic actin forms (β- and γ-actin). The actin present here is the γ-chain of the cytoplasmic actin form.

An enzyme of the citric acid cycle and of the malate-aspartate shuttle, malate dehydrogenase, was also identified. Malate dehydrogenase occurs in animal tissue in a cytosolic and a mitochondrial isoform. Both isoenzymes, in cooperation with aspartate aminotransferase, play an important part in the malate-aspartate shuttle between cytosol and mitochondrium.

The 22 kDa protein of fraction (5) was assigned to two proteins on the basis of the sequenced peptide fragment: the macrophage 23 kDa stress protein ("MSP23") also known as osteoblast-specific factor 3 ("OSF-3") and the "natural killer cell enhancing factor-A" ("NKEF-A"). Activated macrophages produce reactive oxygen compounds such as $H_2O_2$ and $O_2$. Since they themselves withstand this oxidative stress, they must have an effective defense system in order to be able to protect themselves from these reactive compounds. NKEF is a cytosolic protein from human red blood cells which increases the activity of the natural killer cells. These are lymphocytes and, after cytokine stimulation, are able to recognize and to destroy a large number of tumor cells. The "natural killer cell enhancing factor" has a molecular weight of 44 kDa and consists of two subunits of equal size (NKEF-A and NKEF-B), which mutually have a good sequence homology of 88%.

EXAMPLE 11
Comparative Affinity Chromatography of Unstimulated, LPS-stimulated and LPS-stimulated, Leflunomide-treated RAW 264.7 Cytosol Extracts The stimulation of the macrophage cell line RAW 264.7 with lipopolysaccharide was used as an in vitro model for inflammatory processes. Lipopolysaccharide ("LPS") is an essential structural constituent of the outer membrane of Gram-negative bacteria and is recognized as such by immune cells of almost all organisms. In particular, macrophages are activated by LPS stimulation to synthesize a number of cytokines such as TNF-α, IL-1 and IL-6. Potential changes in the protein pattern which accompany this stimulation should be prevented by the simultaneous administration of the immunoregulatory preparation leflunomide.

RAW 264.7 cells were incubated with 10 ng of LPS/ml of culture medium for 24 hours. In the case of LPS-stimulated, leflunomide-treated cells, incubation was simultaneously carried out with 60 $\mu$M A 77 1726B for 24 hours. The cells were processed and the cytosolic extracts investigated by affinity chromatography with the aid of the FRACTOGEL® column derivatized according to Example 10. The preparation fractions of these three batches were then applied to an analytical gradient gel and compared with one another.

The increase in a band around 35 kDa, which had already been identified by sequencing as malate dehydrogenase, was particularly clearly defined. In comparison with the other protein bands, which tended to be weaker in their intensity on incubation with LPS and A 77 1726B, the intensity of these bands markedly increased.

What is claimed is:

1. A compound of the formula IV

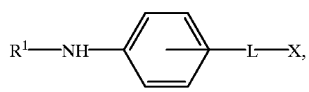

(IV)

where $R^1$ is the radical of the formula II

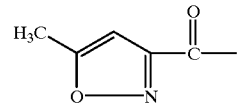

(II)

L is a bridging member from the group
  a) —O—,
  —NH—,
  c) —O—$(CH_2)_n$—$CH_2$—, in which n is the integer 1, 2, or 3,
  d) —NH—C(O)—CH—$(R^4)(R^3)$,
    in which $R^3$ is
      a) a covalent bond or
      b) —NH— and $R^4$ is
      a) a hydrogen atom or
      b) a radical of an amino acid, or
  e) a bridging member L, defined as under a) to d), which has a spacer, in which the spacer is a radical of the group
    1) —NH—$(CH_2)_m$—S—, in which m is an integer from 1 to 12, and X is a polymer or solid.

2. The compound as claimed in claim 1, wherein the polymer is synthetic or natural polymers from the group consisting of polystyrene, polypropylene, polyvinyl chloride, latex, polysaccharides, SEPHAROSE, proteins, lipids, silicates, or nucleic acids.

3. The compound as claimed in claim 1, wherein the solid is a tube, beads, or a microtiter plate.

4. A method for isolating a binding protein comprising the steps of:
  a) obtaining a compound of the formula IV as claimed in claim 1,
  b) obtaining a sample from a cell extract, serum, blood, or synovial fluid,
  c) mixing the sample of step (b) with the compound of step (a),
  d) removing unbound sample, and
  e) isolating the binding protein.

5. The method according to claim 4, further comprising the step of modifying a microtiter plate with the isolate binding protein.

6. The method according to claim 5, wherein the chromatography material is affinity chromatography material.

7. The method according to claim 4, further comprising the step of attaching the isolated binding protein to the surface of a microtiter plate.

8. A method for detecting the presence of a disease comprising the steps of:
  a) binding an analyte indicative of said disease with a compound of the formula IV as claimed in claim 1, and
  b) detecting the presence of said analyte which is indicative of said disease.

* * * * *

UNITED STATES PATENT AND TRADEMARK OFFICE
CERTIFICATE OF CORRECTION

PATENT NO. : 6,265,588 B1
DATED : July 24, 2001
INVENTOR(S) : Stefan Müllner et al.

It is certified that error appears in the above-identified patent and that said Letters Patent is hereby corrected as shown below:

Title page,
Item [57] ABSTRACT,
Line 2, in the formula of Fig. (I), "$R_2$" should read -- $R^2$ --.

Column 18, claim 1,
Line 12, "–NH–," should read -- b) –NH–, --.

Signed and Sealed this

Second Day of April, 2002

Attest:

JAMES E. ROGAN
*Attesting Officer*     *Director of the United States Patent and Trademark Office*